United States Patent
Turner et al.

(10) Patent No.: US 9,347,084 B2
(45) Date of Patent: *May 24, 2016

(54) SCREENING FOR PROTEIN VARIANTS USING MASS SPECTROMETRY

(71) Applicants: King's College London, London (GB); Guy's & St. Thomas' NHS Foundation Trust, London (GB)

(72) Inventors: Charles Turner, London (GB); Raymond Neil Dalton, London (GB); Yvonne Anne Daniel, London (GB)

(73) Assignees: King's College London, London (GB); Guy's St. Thomas' NHS Foundation Trust, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/187,911

(22) Filed: Feb. 24, 2014

(65) Prior Publication Data

US 2014/0212906 A1 Jul. 31, 2014

Related U.S. Application Data

(63) Continuation of application No. 11/883,463, filed as application No. PCT/GB2006/000328 on Feb. 1, 2006, now Pat. No. 8,658,396.

(30) Foreign Application Priority Data

Feb. 1, 2005 (GB) .................................. 0502068.0

(51) Int. Cl.
*C12Q 1/37* (2006.01)
*G01N 33/68* (2006.01)
*G01N 33/72* (2006.01)

(52) U.S. Cl.
CPC .............. *C12Q 1/37* (2013.01); *G01N 33/6848* (2013.01); *G01N 33/721* (2013.01); *G01N 2333/976* (2013.01); *G01N 2560/00* (2013.01)

(58) Field of Classification Search
CPC ................................................. G01N 33/6848
See application file for complete search history.

(56) References Cited

U.S. PATENT DOCUMENTS 6,285,027 B1    9/2001   Chernushevich et al.

FOREIGN PATENT DOCUMENTS

| JP | 2005-522713 | 7/2005 |
| JP | 2005-536729 | 12/2005 |
| WO | 03/078962 | 9/2003 |
| WO | 2005/100973 | 10/2005 |

OTHER PUBLICATIONS

Wild et al., "The potential of electrospray ionization mass spectrometry for the diagnosis of hemoglobin variants found in newborn screening," Blood Cells, Molecules & Diseases, 33 (2004) 308-317.

Reynolds et al., "Hemoglobin Wayne in a British Family: Identification by Electrospray Ionization/Mass Spectrometry," Clinical Chemistry48, No. 12, 2002, pp. 2261-2263.
Wild et al., "Rapid Identification of Hemoglobin Variants by Electrospray Ionization Mass Spectrometry," Blood Cells, Molecules, and Diseases (2001) 27(3), May/June, pp. 691-704.
Rai, "The Use of Mass Spectrometry and DNA Technology in Investigation of Hemoglobin Disorder," 2003 PhD Thesis of Dilip K. Rai, Department of Laboratory Medicine, Huddinge University, Stockholm.
Griffiths et al., "Electrospray and tandem mass spectrometry in biochemistry," Biochem. J. (2001), 355, pp. 545-561.
Protein Sequencing and Identification Using Tandem Mass Spectrometry (2000, John Wiley InterScience ISMB 0-471-32249-0, Kinter Sherman).
Dalton et al., "Clinical Applications of Mass Spectrometry," Advances in Mass Spectrometry, vol. 16, 2004, pp. 315-321.
Yang et al., "Evaluation of a Four-Channel Multiplexed Electrospray Triple Quadrupole Mass Spectrometer for the Simultaneous Validation of LC/MS/MS Methods in Four Different Preclinical Matrixes," Anal. Chem. 2001, 73, pp. 1740-1747.
Larsen et al., "Collision-induced dissociation of glycero phospholipids using electrospray ion-trap mass spectrometry," Rapid Communications in Mass Spectrometry, 2001, 15:2393-2398.
Shackleton et al., "Mass-Spectrometry in the Characterization of Variant Hemoglobins," Extract from Mass Spectrometry: Clinical and Biomedical Applications, vol. 2, 1994, Plenum Press.
Rai et al., "Electrospray tandem mass spectrometry of intact beta-chain hemoglobin variants," Anal. Chem., 2002, 74:2097-2102.
Li et al., "Tandem mass spectrometry for the direct assay of enzymes in dried blood spots: application to newborn screening for Krabbe disease," Clinical Chemistry, 2004, 50(3):638-640.
Fujita et al., "Hemoblobin A2 Honai (α2•290(F6)GLU-VAL): A New Delta Chain Variant," Hemoglobin, 1985, 9(6):597-607.
Simizu et al., "Diagnosis of protein abnormality by mass spectrometry," Medical Technology; vol. 31, No. 11, Nov. 2003, pp. 1225-1232.
Nakanishi et al., "Assignment of the ions in the electrospray ionization mass spectra of the tryptic digest of the non-derivatized globin, covering the whole sequence of alpha- and beta-chains: a rapid diagnosis of haemoglobinopathy," J. Mass. Spec., 1995, 30:1663-1670.
Schindler et al., "Characterization of beta-Asp33 isoform of recombinant Hirudin sequence variant 1 by lower-energy collision-induced dissociation," J. of Mass Spectrom., 1996, 24:967-974.

(Continued)

*Primary Examiner* — Bin Shen
(74) *Attorney, Agent, or Firm* — Banner & Witcoff, Ltd.

(57) ABSTRACT

A method for screening for variant peptides uses mass spectrometry (MS). A system and a kit may be used for performing the method. Proteins in a sample are digested to form a defined series of peptides. The defined series of peptides are ionized. The ionized species are subjected to collision induced dissociation. Species of known mass/charge ratio are detected to confirm the presence of the protein variant in the original sample.

16 Claims, 7 Drawing Sheets

(56) References Cited

OTHER PUBLICATIONS

Li et al., "The used of on-line capillary electrophoresis/electrospray ionization with detection via an ion trap storage/reflectron time-of-flight mass spectrometer for rapid mutation-site analysis of hemoglobin variants," Rapid Commu. in Mass Spectrom., 1997, 11:99-108.

Cao et al., "Pressure-assisted and pressure-programmed capillary electrophoresis/electrospray ionization time of flight-mass spectrometry for teh analysis of peptide mixtures," Electrophoresis, 1998, 19:2200-2206.

Daniel et al., "Rapid and specific detection of clinically significant haemoglobinopathies using electrospray mass spectrometry-mass spectrometry," British Journal of Haematology, Aug. 2005, vol. 130, No. 4, pp. 635-643.

Avidity IP, Grounds of Appeal submitted in Opposition of corresponding European Patent No. 1844338 (06703925.5), May 22, 2014, Munich Germany, pp. 1-9.

Anderson, Leigh, Candidate-based proteomics in the search for biomarkers of cardiovascular disease, J Physiol. 563.1 (2005) pp. 23-60—first published online Dec. 20, 2004.

Willakans, Quantification of Glycohemoglobin in Blood by Mass Spectrometry Applying Multiple Reaction Monitoring, Clinical Chemistry 46, No. 2, 2000 (p. 25 of the Micromass Quattro II User's Gude).

SCREENING FOR PROTEIN VARIANTS USING MASS SPECTROMETRY

The present invention relates to a method for screening for variant peptides using mass spectrometry (MS). The present invention also relates to a system and a kit for performing the method.

Mass spectrometry has proven to be a most valuable tool for the determination of molecular structures of molecules of many kinds, including biomolecules, and is widely practised today. The technique involves bombardment of the molecular species under examination with electrons or other high energy particles which cause the ionisation and fragmentation of the molecule, resulting in a wide spectrum of ionised particles of varying charge and mass. Soft-ionisation techniques, such as electrospray, result in ionisation but do not primarily cause fragmentation of molecules. The technique is particularly valuable in producing multiply-charged species of proteins and peptides. The complex mass/charge spectra produced are, as conventionally practised, converted into a computer-generated deconvoluted spectrum having a single mass peak for each polypeptide. Current developments of mass spectrometry have centred largely around developing the most effective software necessary for deconvolutional analysis. In spite of continuing improvements in this part of the technique, however, this remains the most demanding and time-consuming component of the procedure for every particular determination. The use of deconvolutional analysis has become indispensable in mass spectrometry aimed at the elucidation of previously unknown or uncertain molecular structures but it proved difficult to simplify the current methodology to significantly reduce the time required for its performance.

Mass spectrometry is also used for the detection of variant proteins and polypeptides implicated in serious diseases. For example, many variant or mutant forms of the polypeptide sub-units of haemoglobin are known to result in various forms of anaemia, and many such mutations are of only one amino acid. The basic molecular structure and amino acid sequences of these proteins, and the corresponding mutations in the DNA encoding them, are already of record in the literature. Masspectrometry has also been used for population screening of inherited metabolic disorders (IMD) (Chase et al., Clin. Chem., 49, 1797-1817, 2003).

In humans the haemoglobinopathies are the commonest inherited disorders. These result from mutations to the globin genes and over 800 haemoglobin variants have been characterised (Huisman et al, Human Haemoglobin Variants, 2nd Edn., Augusta, Ga.: Sickle Cell Anemia Foundation 1998), many of which are of no clinical significance. Haemoglobin variants are usually detected as a result of pre-anaesthetic screening or neonatal and ante-natal screening programmes. Variants that result in clinical symptoms may also be identified as part of diagnostic investigations. Recent health initiatives, which have expanded existing neonatal and ante-natal screening programmes, have dramatically increased workload (The NHS Plan July 2000, command paper 4818). They have also led to a requirement for testing systems specific for those haemoglobin variants deemed clinically significant. The two programmes have different objectives. In ante-natal screening the aim is to identify carriers of those haemoglobinopathies which pose a genetic risk to the foetus. Thus the aim is to detect the presence or absence of sickle haemoglobin and beta thalassaemia trait or one of the haemoglobin variants that interact with them, e.g., Hb C, Hb D$^{Punjab}$, Hb O$^{Arab}$, Hb Lepore and Hb E. In addition three other conditions of potential clinical significance namely delta beta thalassaemia, hereditary persistence of foetal haemoglobin trait (HPFH) and alpha zero thalassaemia trait are also included. In neonatal screening the aim is early identification of individuals with sickle cell disease and beta thalassaemia major in order to initiate treatment.

Classical biochemical diagnosis of haemoglobinopathies uses phenotypic information generated by either electrophoretic techniques or cation-exchange chromatography (Working Party Of General Haematology Task Force, 1998). These form the basis of current screening techniques; however, they are slow, laborious and non-specific. Furthermore, they are not targeted and thus will detect haemoglobin variants not required by the screening programmes. Electrospray quadrupole mass spectrometry (MS) is potentially faster, more specific and is more cost effective for population screening.

Most published methods for the characterisation of haemoglobinopathies using MS have used whole blood scans to assess the masses of the intact globin chains followed by tryptic digestion and analysis of the peptides (Wild et al. Blood Cells, Molecules and Diseases, 27, 691-704, 2001). In this way it is possible to unequivocally characterise the majority of globin mutations.

Reference is made to Wild et al., 2001, (supra) for details of the MS procedure, in particular the methods section on page 693 and FIG. 2, page 697 that shows deconvoluted ESI mass spectra for the normal and one particular variant β haemoglobin chain. Table 1 on page 698 of Wild et al., 2001, (supra) lists many mass and amino acid changes produced by single base changes in the nucleotide coding triplet and which are determinable by the MS method.

In International Patent Application WO 2004/090552 a simplified MS procedure is used to detect the presence of a sickle cell protein mutation of the β-globin chain. By working from knowledge of the normal (wild-type) polypeptide and its mutant, MS is focused on charged species and the recording and analysis of all other data is avoided. It is therefore possible to detect a single targeted ionised species and to detect a peak corresponding to the variant if present in the sample tested. The method is referred to as one of targeting specific selected ionised species. Related methods are also described in Shushan et al., Clinical Chemistry, 44, A150, 1998; Liu Tao et al., Shengwu Huaxue Yu Shengwu Wuli Xuebao, 34, 423-432, 2002; Kobold et al., Clinical Chemistry, 43, 1944-1951, 1997; Wan et al., J. Chromatog., 913 437-446, 2001; and Van Dorsselaer et al., Biochemistry, 28 2949-2956, 1989.

There are still a number of problems with the prior art methods, including that the targeted ionised species being detected may be confused with a species having the identical mass/charge ratio, and a lack of sensitivity. Furthermore, when a protein variant differs in a very minor way from the wild-type protein, it can be very difficult to distinguish between the variant and the wild-type protein using MS.

The present invention relates to a more sensitive method for screening for protein variations. Increased sensitivity is particularly important when the variant protein is in a sample obtained from an individual who is heterozygous for the variant protein.

The present invention provides a method for detecting a known protein variant in a sample comprising:
  (i) digesting the protein to produce a defined series of peptides;
  (ii) ionising the peptides and selecting by mass spectrometry an ionised species of known mass/charge ratio indicative of the protein variant; and
  (iii) subjecting the selected ionised species to collision induced dissociation and measuring one or more of the derived ionised species of known mass/charge ratio that confirms the presence of the protein variant in the sample.

The method of the present invention allows the accurate and specific detection of a protein variant. In particular, by digesting the protein to produce a defined series of peptides and by subjecting the selected ionised species to collision induced dissociation, there is considerably less chance of the method detecting a false positive.

The method of the present invention can be used to detect any protein variant such as a protein mutation or an abnormal concentration of a wild-type protein. Any inherited disorder leading to variant protein production may therefore be detected using the present invention. Particular protein variants that can be detected with the method of the present invention include haemoglobin variants and variant proteins associated with congenital disorders of glycosylation (CDG). Variant haemoglobin proteins that cause various forms of anaemia can be found described in standard textbooks, including 'Clinical Genetics' by Golder N. Wilson, Wiley Liss (2000) at pages 114-119. Wild et al., 2001 (supra) also lists many such amino acid changes at page 698 thereof. All such variations are amenable to detection in accordance with the present invention. It is particularly preferred that the method of the present invention is used to detect clinically important haemoglobin variants such as Hb S, Hb C, Hb $D^{Punjab}$, Hb $O^{Arab}$, Hb Lepore, Fib E, delta beta thalassaemia, hereditary persistence of foetal haemoglobin trait (HPFH) and alpha zero thalassaemia trait. It is further preferred that the method of the present invention is used to detect the following clinically important haemoglobin variants: S, C, E, $D^{Punjab}$, and $O^{arab}$.

The protein variant to be detected may be any protein including a glycoprotein. In particular, specific glycoproteins indicative of a metabolic disorder may be detected using the method of the present invention. For example, congenital disorders of glycosylation (CDG) are usually diagnosed by analysis of plasma transferrin, a normally heavily gycosylated plasma protein, which displays characteristic patterns of under-incorporation of sugar moieties depending on the precise CDG type. The protein variant to be detected may be any protein indicative of a disorder or a disease. For example: albumin in urine, which is considered a marker of endothelial damage in the kidney and therefore a marker of risk of progression of renal disease and cardiovascular damage; low molecular weight proteins in urine (e.g. retinol binding protein), elevated levels of which indicate kidney tubule damage; prion protein (PrP) variants in CSF may indicate inherited spongiform encephalopathies; and pancreatic proteins in blood might allow screening for cystic fibrosis.

The method is used to detect a known protein variant. Accordingly, the sequence of the protein variant to be detected must be known. This is important as the method requires the selection of an ionised species of known mass/charge ratio derived from the protein. If the variant being detected is not known then it is not possible to determine the mass/charge ratio of the ionised species derived from the protein.

The term "ionised species" refers to a peptide that has been ionised and is therefore charged.

By selecting an ionised species of known mass/charge ratio, only a limited window of mass/charge ratios needs to be scanned. This reduces considerably the amount of work and analysis that needs to be performed by the operator. In particular, by selecting a single ionised species of known mass/charge ratio, a wide spectrum of ionised particles having different mass/charge ratios does not need to be determined and the complicated and time consuming step of deconvolution analysis does not need to be performed. By avoiding these time consuming steps, the methods can be used to determine the presence of the protein variant quickly and accurately.

In some situations the method may be used to select a small number of ionised species of known mass/charge ratio. The small number of ionised species may be from 1 to 20, preferably 1 to 10, more preferably 1 to 5. Even when the method comprises selecting a small number of ionised species of known mass/charge ratio, the method will be considerably faster and less complicated than the prior art methods where a wide spectrum of ionised particles is determined. It is most preferred that the method comprises selecting a single ionised species have a known mass/charge ratio.

The sample in which the protein variant is detected can be any suitable sample, such as blood, urine, cerebrospinal fluid and tissue samples. Obviously the type of sample will depend on the protein variant to be detected. If the protein variant is a haemoglobin variant, the sample is preferably blood. Furthermore, it has been found that blood spots can be used as samples. The sample may be processed by standard methods to remove any undesired contaminants, to concentrate the protein variant to be detected, to denature the protein and/or to place the sample in a form suitable for protein digestion. Suitable methods for processing the sample are well known to those skilled in the art.

The protein is digested to produce a defined series of peptides. The term "a defined series of peptides" means that the series of peptides produced by digesting the protein can be predicted. For example, when using a sequence specific protease (i.e. a protease that cleaves at a specific sequence) such as trypsin, the series of peptides produced can be predicted based on the sequence of the protein.

By digesting the protein to produce a series of peptides, one or more of the peptides will be specific for the protein variant to be detected. For example, if the variant protein differs from the wild-type protein (non-variant protein) by a single amino acid, the peptide comprising the variant amino acid will be indicative of the variant protein. Alternatively, if the variant protein differs from the wild-type protein in a way such that a site of cleavage for a particular protease changes, one or more new peptides will be produced, and the one or more new peptides will be indicative of the variant protein.

The protein variant may be a wild-type protein that differs to a related protein. Again, any difference between the proteins can be used to specifically detect the protein variant.

The defined series of peptides are ionised and an ionised species of known mass/charge ratio that is indicative of the protein variant is selected. The peptides can be ionised and the ionised species selected using any method of mass spectrometry known to those skilled in the art. In a preferred embodiment, electrospray ionisation quadrupole mass spectrometry is used to ionise the peptides and to select the ionised species. It will be appreciated by those skilled in this general field of technology that other ionisation methods, particularly soft ionisation techniques, e.g. fast atom bombardment (FAB) and matrix assisted laser desorption ionisation (MALDI), and other mass analysis systems, e.g. time-of-flight (TOF) and magnetic sector, are also possible.

As the specific ionised peptide to be selected is known, it is possible to predict the mass/charge ratio of the ionised species to be selected by mass spectrometry. As will be apparent to those skilled in the art, a particular peptide will, depending on the degree of ionisation, form a number of ionised species that have different mass/charge ratios. One or more of the ionised species can be selected. The ionised species to be selected will depend on a number of variables, including ease of fragmentation and ability to distinguish derived ionised species from those derived from the non-variant protein, but should be chosen in order to obtain the optimum level of detection.

As indicated above, the ionised species selected will be indicative of the protein variant as it will either be produced from a peptide having a variant amino acid sequence (i.e. the amino acid sequence of the peptide will differ to the corresponding peptide obtained from the wild-type (non-variant) protein), or it will be produced from a peptide only formed when the variant protein is digested (i.e. the variant protein has a different site of cleavage on digestion compared to the wild-type (non-variant) protein).

The selected ionised species is only indicative of the variant protein as there may be an unrelated ionised species having the same mass/charge ratio. The unrelated ionised species may be formed from a different protein present in the sample or may be formed from a different part of the variant or non-variant protein.

In view of this and in order to improve the accuracy of the method, the selected ionised species is subjected to collision induced dissociation and one or more derived ionised species of known mass/charge ratio are measured. The selected ionised species can be ionised and measured using any method of mass spectrometry known to those skilled in the art. Preferred methods are indicated above.

On subjecting the selected ionised species to collision induced dissociation, two things can happen.

Firstly, the selected ionised species is dissociated to give a plurality of ionised peptide fragments. The series of ionised peptide fragments can be measured to identify an ionised species of known mass/charge ratio. It is possible to predict what ionised species will be produced on dissociation of the selected ionised species if the selected ionised species is derived from the protein variant. The mass/charge ratio can also be predicted. Accordingly, by looking for the ionised species following dissociation it is possible to confirm the presence of the protein variant in the sample.

Secondly, the selected ionised species is not dissociated to give a plurality of ionised peptides. However, any contaminating isobaric peptides may be dissociated. The selected ionised species can therefore be measured and will confirm the presence of the protein variant in the sample.

Accordingly, the one or more derived ionised species may be identical to the originally selected ionised species or may be ionised fragments thereof. For example, the originally selected ionised species may be dissociated into 2 or more smaller ionised peptide species.

The level of collision induced dissociation can be varied and thereby the degree of dissociation of the selected ionised species can be controlled. In a preferred embodiment of the present invention the selected ionised species is subjected to:
1. low energy fragmentation that either does not cause substantial dissociation of the selected ionised species or leads to the production of a plurality of ionised peptide fragments (low level fragmentation); and 2. high energy fragmentation that causes the removal of amino acids from both ends of the ionised species (high energy fragmentation). The detection of the amino acids therefore enables one skilled in the art to determine the sequence of the selected ionised species.

By additionally performing high energy fragmentation further information concerning the identity of the selected ionised species is obtained. This additional information provides further confirmation of the presence of the protein variant in the sample.

Accordingly, it is preferred that the method of the present invention additionally comprises subjecting the selected ionised species to high energy fragmentation so that amino acids from both ends of the ionised species are removed and the sequence of the ionised species is determined.

The low and high energy fragmentation levels of collision induced dissociation can be performed simultaneously or sequentially. Preferably the low and high energy levels of collision induced dissociation are performed simultaneously. There are a number of Mass Spectrometers available that are capable of performing low and high energy fragmentation simultaneously. In particular, any Mass Spectrometer having a linear ion trap can be used, such as the API 2000 Q-trap or the Q-trap 4000 (SCIEX).

The present invention also provides a system for performing the method of the present invention, wherein the system comprises a machine for performing tandem mass spectrometry set up for performing the method of the present invention.

The present invention also provides a kit for performing the method of the present invention, wherein the kit comprises:
  (i) buffers and reagents for preparing the protein sample;
  (ii) a protease for digesting the protein sample into a series of defined peptides;
  (iii) a carrier substrate for delivering the sample to a machine for performing tandem mass spectrometry; and
  (iv) a machine for performing tandem mass spectrometry set up for performing the method of the present invention.

The kit may additionally comprise software suitable for setting up the machine for performing the method of the present invention.

The present invention is now described by way of example only refers to the following Figures.

FIG. 1 shows the mass scans m/z 100-1500 of tryptic digests of blood from a control subject with normal beta haemoglobin (A) and a patient with sickle cell disease (B). The insets emphasise the complexity of raw spectra. The arrows reveal zoomed spectra for the informative [M+2H]2+ and [M+1H]+ ions for control (A) and sickle patient (B), respectively. Note the mass shift of −30 Da for the [M+H]+ ions and −Da for the [M+H]+ ions.

EXAMPLES

The inventors have developed a targeted approach to specifically identify important protein variants, especially globin variants. This utilises the fact that the mutation responsible for each of the variants described is known and thus from the genetic code the amino acid sequence can be determined. The process of digestion with trypsin cleaves the globin chain, at the points in the chain where arginine and lysine occur, into a series of peptides. A tandem Mass Spectrometer (API 4000, MDS-SCIEX) allows selection of the peptides and collision induced fragmentation such that an ionised species specific to the mutation can be detected. Mutations that alter cleavage sites, by adding or replacing arginine and lysine, generate peptides that are specific if a single mutation is present.

The inventors have performed a series of MSMS and pseudo MSMS experiments to investigate the three important peptides formed during tryptic digestion of beta globin, T1, T3 and T13 that include the mutations associated with Haemoglobin S, C, E, $D^{Punjab}$ and $O^{Arab}$. The protocol looks for ionised products specific to haemoglobin S and haemoglobin C, $D^{Punjab}$, $O^{Arab}$ and E. An ionised species specific for the mass of the normal Beta T1 chain and ionised species corresponding to the normal T3 and T13 peptides are also measured. This was used as a quality control check for the analytical procedure and to determine carrier or disease status for the mutations.

Haemoglobin S

Haemoglobin S is formed as a result of a substitution of the amino acid valine for the wild type glutamic acid at position 6 of the beta chain. This leads to a product with a mass of 30 Daltons (Da) less than that of wild type. When subjected to digestion with trypsin the sickle mutation is located in the T1 fragment, which contains the first eight amino acids of the beta chain. The amino acid sequence and molecular mass is shown in table 1.

TABLE 1

Beta T1 Fragment Amino Acid Sequence with Molecular Mass

| Position | Amino Acid | Abbreviated Forms | One Letter Code | Molecular Mass (Da) |
|---|---|---|---|---|
| 1 | Valine | Val | V | 117.1 |
| 2 | Histidine | His | H | 155.2 |
| 3 | Leucine | Leu | L | 131.2 |
| 4 | Threonine | Thr | T | 119.1 |
| 5 | Proline | Prol | P | 115.1 |
| 6 | Glutamic Acid | Glu | E | 147.1 |
| 7 | Glutamic Acid | Glu | E | 147.1 |
| 8 | Lysine | Lys | K | 146.2 |

Figure 1:
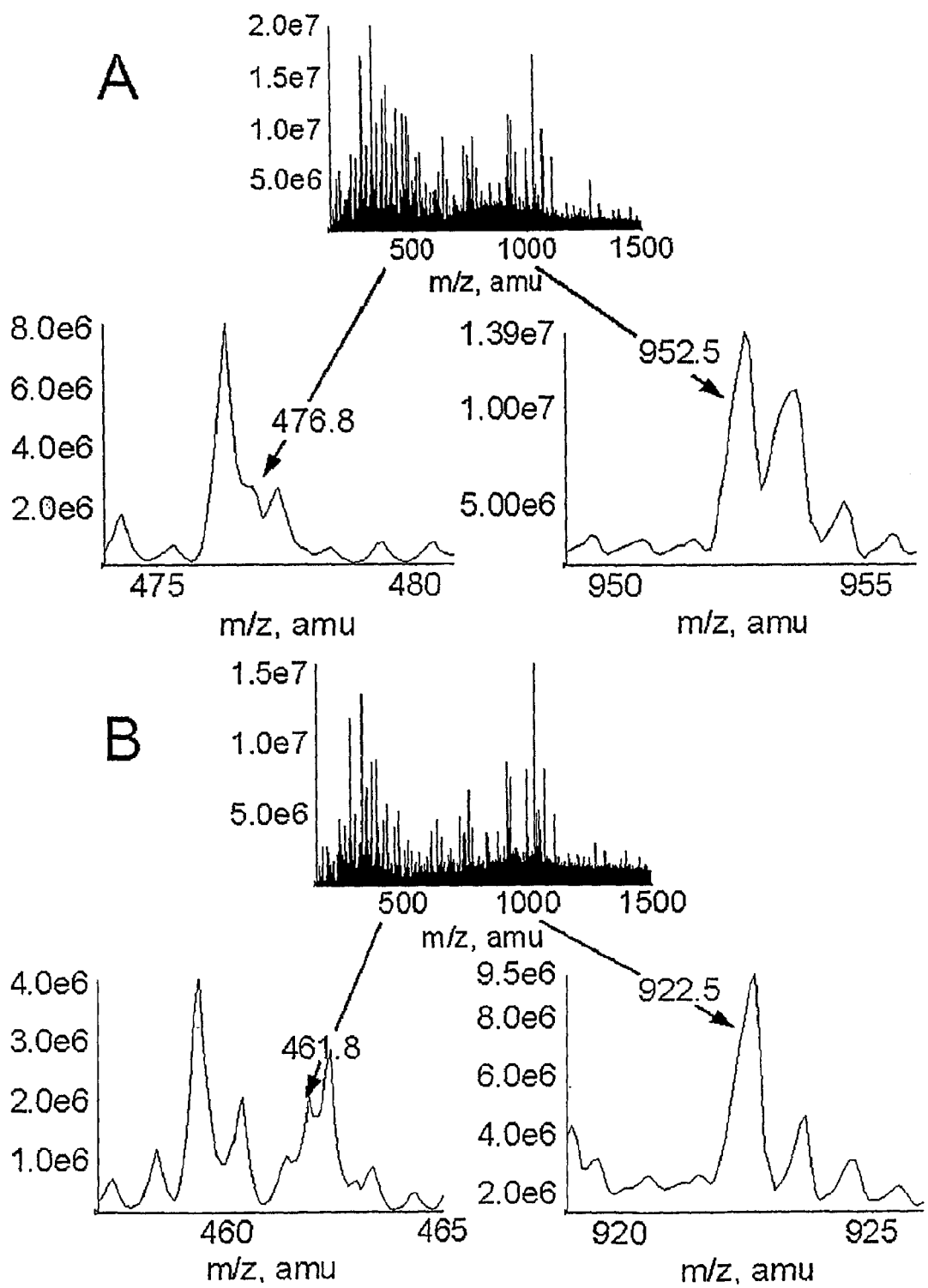

Using an electrospray MSMS strategy a peptide is ionised to produce a series of multiply charged ionised species. The theoretical mass/charge ratio of the singly charged wild-type beta chain T1 peptide is [M+H]+ 952.5 and of the doubly charged peptide [M+H]2+ 476.8. Both species are observed on a m/z 100-1500 scan of an appropriate digest (FIG. 1A). In a sample from a patient with sickle cell disease the substitution of the glutamic acid at position 6 with valine produces equivalent charged peptides [M+H]+ 922.5 and [M+H]2+ 461.8 (FIG. 1B) and the wild-type ions are absent. Therefore, the 30 Da mass reduction from wild-type beta chain has been isolated to the T1 peptide. This is highly specific, but a further level of specificity and background reduction can be introduced by using collision induced dissociation (CID) or fragmentation of the T1 peptide. According, the peptide of interest is isolated in quadrupole 1 (MS 1) subjected to collision induced dissociation in quadrupole 2 and analysed in quadrupole 3 (MS 2).

Fragmentation of doubly charged peptides usually results in the production of two complementary peptide ions, termed the y ion and b ion. The y ion retains a positive charge at its C terminal end, whilst the b ion retains the positive charge at the N terminal end. Thus from knowing the amino acid sequence of a peptide it is possible to calculate the fragmentation mass of the resulting ions. This is shown for the normal and sickle T1 peptide in the tables 2 and 3.

TABLE 2

Wild Type Beta T1 Fragmentation Table

| Position | Wild Type Amino Acid Sequence | b ion | | y ion | Peptide Molecular Mass (Da) |
|---|---|---|---|---|---|
| 1 | V | b1 | 100.1 | | 99.0684 |
| 2 | H | b2 | 237.2 | y7 | 853.4 | 137.0589 |
| 3 | L | b3 | 350.3 | y6 | 716.3 | 113.0841 |
| 4 | T | b4 | 451.3 | y5 | 603.2 | 101.0477 |
| 5 | P | b5 | 548.4 | y4 | 502.2 | 97.0528 |
| 6 | E | b6 | 677.4 | y3 | 405.1 | 129.0426 |
| 7 | E | b7 | 806.4 | y2 | 276.1 | 129.0426 |
| 8 | K | | | y1 | 147.1 | 128.0949 |
| Total | | | | | | 933.492 |

Theoretical Mass (M) = Total peptide mass + $H_2O$ = 951.492 Da
[M + H] = 952.5 Da
[M + 2H] = 476.8 Da

TABLE 3

Sickle Beta T1 Fragmentation Table

| Position | Sickle Amino Acid Sequence | b ion | | y ion | | Peptide Molecular Mass (Da) |
|---|---|---|---|---|---|---|
| 1 | V | b1 | 100.1 | | | 99.0684 |
| 2 | H | b2 | 237.2 | y7 | 823.5 | 137.0589 |
| 3 | L | b3 | 350.3 | y6 | 686.4 | 113.0841 |
| 4 | T | b4 | 451.3 | y5 | 573.3 | 101.0477 |
| 5 | P | b5 | 548.4 | y4 | 472.3 | 97.0528 |
| 6 | V | b6 | 647.5 | y3 | 375.2 | 99.0684 |
| 7 | E | b7 | 776.5 | y2 | 276.1 | 129.0426 |
| 8 | K | | | y1 | 147.1 | 128.0949 |
| Total | | | | | | 903.5178 |

Theoretical Mass (M) = Total peptide mass + $H_2O$ = 921.518 Da
[M + H] = 922.5 Da
[M + 2H} = 461.8 Da We developed and optimised a protocol for the mass spectrometer in use which selects the [M+2H] peptide mass to identify the peptide of interest in the first quadrupole. This is fragmented in the collision cell with subsequent identification of the ionised peptide fragments in the second quadrupole. By this method, for the y ion the selected mass for a normal beta T1 fragment is 476.8 Da with the y4 ion of 502.3 Da as the target product. The selected mass for the sickle T1 fragment is 461.9 Da with the y4 ion of 472.4 Da as the target product.

Figure 2:
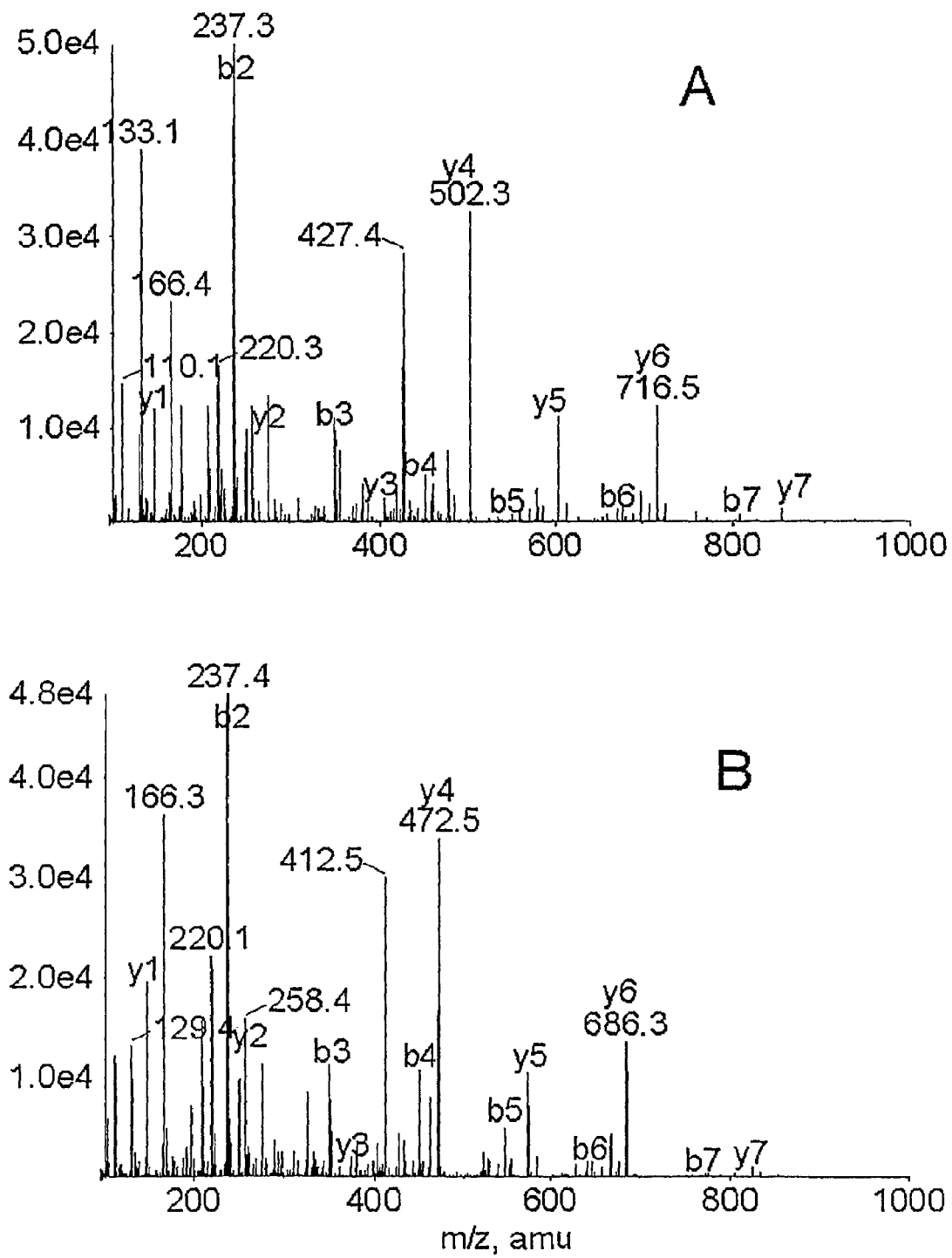
FIG. 2 shows the product ion scans of control beta haemoglobin T1 peptide [M+2H]2+, m/z 476.8 (A) and haemoglobin S T1 peptide [M+2H]2+, m/z 461.8 (B). Note the y and b series fragments that provide unequivocal sequence data and the y4 MRM target ions, m/z 502.3 and 472.3, respectively.

Product ion scans of wild-type (FIG. 2A) and sickle (FIG. 2B) [M+2H]2+ ions demonstrate the practicality of the approach. Note that the [M+2H]2+ ions were used because they fragment at lower collision energies 10. The scan of the sickle protein is unique and essentially diagnostic. However, for population screening of multiple mutations targeting a peptide of interest provides the opportunity to use the instrument in the high sensitivity multiple reaction monitoring (MRM) mode. In the case of sickle protein the theoretically most specific target is the y3 ion. In practice, because of the proline effect at position 5 (Williams et al., Biochem. J., 201, 105-117, 1982) the y4 ion (m/z 472.3) provides a much more sensitive signal. The theoretical wild-type MRM is m/z 476.8/502.2 and for sickle protein m/z 461.8/472.3.

The method for identification of sickle protein involves tryptic digestion of whole blood, automated direct injection of the digest, 2 MRM acquisitions, and an inject-to-inject time of approximately 1 minute. Unequivocal confirmation can be made using a second injection of the tryptic digest and product ion scanning of the peptide of interest to provide sequence information.

The above approach has been used for the haemoglobinopathies below.

Haemoglobin C

Haemoglobin C is formed as a result of a substitution of the amino acid lysine for the wild type glutamic acid at position 6 of the beta chain. When subjected to digestion with trypsin this creates a new cleavage point at position 6 and thus a new peptide with a specific mass. This peptide has the amino acid sequence VHLTPK (SEQ ID NO: 1) [M+H] 694.4 Da. In this instance, the specificity of the new peptide renders fragmentation unnecessary for screening. The higher stability of singly charged peptides when compared to doubly charged peptides means that, at the collision energy required for the sickle and wild-type MRMs, the C peptide specific [M+H]+ ion undergoes minimal fragmentation. Thus, a "MRM" m/z 694.4/694.4 can be applied. The same "pseudo-MEM" approach has been used for haemoglobins $D^{Punjab}$, $O^{Arab}$, and E.

Haemoglobin $D^{Punjab}$

Haemoglobin $D^{Punjab}$ is formed as a result of a substitution of the amino acid glutamine for the wild type glutamic acid at position 121 of the beta chain. This leads to a product with a mass of 1 less than wild type. When subjected to digestion with trypsin this is found in the T13 peptide which contains amino acids 121 to 132. Thus the wild type T13 sequence of EFTPPVQAAYQK (SEQ ID NO: 2) is altered to QFTPPVQAAYQK (SEQ ID NO: 3). No other single amino acid substitution in this peptide will cause a mass alteration of minus 1, therefore the mass alteration of the T13 wild type fragment from [M+H] 1378.8 Da to [M+H] 1377.8 is highly specific for haemoglobin $D^{Punjab}$.

Haemoglobin $O^{Arab}$

Haemoglobin $O^{Arab}$ is formed as a result of a substitution of the amino acid lysine for the wild type glutamic acid at position 121 of the beta chain. When digested with trypsin this creates a new cleavage point at position 121 with a new peptide. The wild type T13 peptide of EFTPPVQAAYQK (SEQ ID NO:4) [M+H] 1378.8 Da becomes FTPPVQAAYQK (SEQ ID NO:5) [M+H] 1249.7 Da.

Haemoglobin E

Haemoglobin E is formed as a result of a substitution of the amino acid lysine for the wild type glutamic acid at position 26 of the beta chain. When subjected to digestion with trypsin this is found in the T3 peptide which contains amino acids 18 to 30. The wild type sequence of the T3 peptide is VNVDEVGGEALGR (SEQ ID NO:6) [M+H] 1314.7 Da. When the haemoglobin E mutation is present the sequence is VNVDEVGGKALGR (SEQ ID NO:7) this forms two new peptides VNVDEVGGK (SEQ ID NO: 8) [M+H] 916.8 and ALGR [M+H] 416.3. The smaller peptide is used as the target peptide as it is less likely to be affected by other multiple mutations.

The protocol created for these 5 haemoglobins uses the following masses to identify their presence or absence as well as that of the corresponding wild type peptide.

TABLE 4

Protocol target peptide and ion masses

|  | Target Peptide | Target ion |
|---|---|---|
| Wild Type T1 | 476.8 Da | y4 502.3 Da |
| Haemoglobin S | 461.9 Da | y4 472.4 Da |
| Haemoglobin C | 694.4 Da |  |
| Wild Type T13 | 1378.8 Da |  |
| Haemoglobin $D^{Punjab}$ | 1377.8 Da |  |
| Haemoglobin $O^{Arab}$ | 1249.7 Da |  |
| Wild Type T3 | 1314.7 Da |  |
| Haemoglobin E | 916.8 Da |  |

Materials and Methods

Patient Group 200 anonymised whole blood samples in EDTA consented for haemoglobinopathy diagnosis, were selected to provide significant numbers for each of the variants to be tested and analysed in parallel with existing methods. These comprised 52 haemoglobin AA, 44 haemoglobin AC (C Trait), 57 AS (Sickle Cell Trait), 16 haemoglobin SC (SC Disease), 14 haemoglobin SS (Sickle Cell Disease), 10 haemoglobin AE (E Trait), 2 haemoglobin $AD^{Punjab}$ ($D^{Punjab}$Trait) and 1 sample each of haemoglobin CC (C. Disease), $D^{Punjab}D^{Punjab}$ ($D^{Punjab}$ Disease), EE (E Disease) $AO^{Arab}$ ($O^{Arab}$ Trait), and $O^{Arab}O^{Arab}$ ($O^{Arab}$ Disease).

Materials

Ammonium bicarbonate (A6141), TCPK treated trypsin (T1426) and Formic Acid obtained from Sigma Aldrich, UK. Acetonitrile obtained from Rathburn Chemicals Ltd.

Existing Methods

The Guideline Laboratory Diagnosis of Haemoglobinopathies (Working Party Of General Haematology Task Force, 1998) was taken as minimum standard. The initial haemoglobinopathy screen was performed by high performance liquid chromatography (HPLC) using a Variant™ II operating with $HbA_2$/$HbA_{1c}$ Dual Program kit (Bio-Rad, UK; Hemel Hempstead, UK). Confirmatory tests for provisional haemoglobin identification were made using established methods including sickle solubility test, acid and alkaline gels (Wild, B. J., Bain, B. J., Churchill Livingstone, 9th Ed. 231-268, 2001), polymerase chain reaction (Fodor, F. H., Eng, C. M., Prenat. Diagn., 12, 58-60, 1999) and beta gene sequencing.

Tryptic Digest

Following the method described by Wild et al., 2001 (supra) whole blood sample (10 ul) was diluted in distilled water (490 ul) to create a working solution. Acetonitrile (10 ul) and 1% formic acid (10 ul) were added to 100 ul of the working solution in order to denature the haemoglobin. After standing for 5 minutes at room temperature 1 M ammonium bicarbonate (6 ul) and TPCK treated Trypsin (5 ul) was added. Once the solution had cleared, it was centrifuged and incubated for 30 minutes at 37° C. Following digestion 40 ul of the solution was diluted in 360 ul of 1:1 acetonitrile:water with 0.2% formic acid to create a working solution. The working solution is transferred to a 96 deep-well polypropylene plate (Semat International Ltd, St Albans, UK), and loaded onto an CTC Analytics HTS PAL refrigerated autosampler (Presearch Ltd, Hitchin, UK) for MSMS analysis.

Mass Spectrometry

The haemoglobin variants are analysed simultaneously as three separate protocols each targeting a different ionised peptide.

Samples (2 μl) were automatically introduced into a continuous solvent stream of acetonitrile:water (1:1) containing 0.025% formic acid flowing at 75 μl/min (Agilent 1100 series) into a SCIEX API 4000 (Applied Biosystems, Warrington, UK) triple quadrupole MSMS with an electrospray source in positive ion mode at 5500V and 2500 C. The interface heater was on, declustering potential 81.0V, and entrance potential 10V. The collision gas setting (6.0), collision energy (30V) and exit potential (15.0V) were constant for 3 MSMS experiments. The first experiment targeting wild-type beta globin T1 and the T1 variants, S and C, the second, wild-type T13 and the T13 variants, $D^{Punjab}$ and $O^{Arab}$, and the third, wildtype T3 and the T3 variant, E. The actual MRMs are shown in Table 4; dwell time 150 ms for each transition. The total acquisition time was 60 sec.

Results 200 blood samples were analysed as described. The numbers of samples and predicted result patterns for each of the haemoglobin phenotypes are shown in table 5.

predicted, in disease and compound heterozygote states the wild type peptide was absent. The exception to this was those patients who had undergone transfusion where as would be expected the wild type peptide was present along with that of the variant. Thus using the approach described for the 200 samples analysed there was 100% correlation between results from existing methods and the predicted result patterns for mass spectrometry identification of the variants. In particular, the detection of heterozygote or homozygote haemoglobins S, C, $D^{Punjab}$, $O^{Arab}$, and E was 100% specific and 100% sensitive, in the two hundred samples analysed.

Discussion

The implementation of national screening programmes for haemoglobinopathies has highlighted the need to identify clinically significant haemoglobins in a timely and precise

TABLE 5

Numbers and Predicted result patterns for haemoglobin phenotypes tested

| Hb Phenotype | No. of Samples | Wild Type T1 (502.3 Da) | Hb S (472.4 Da) | Hb C (694.4 Da) | Wild Type T13 (1378.8 Da) | Hb $D^{Punjab}$ (1377.8 Da) | Hb $O^{Arab}$ (1249.7 Da) | Wild Type T3 (1314.7 Da) | Hb E (916.8 Da) |
|---|---|---|---|---|---|---|---|---|---|
| AA | 52 | Present | | | Present | | | Present | |
| AS | 57 | Present | Present | | Present | | | Present | |
| AC | 44 | Present | | Present | Present | | | Present | |
| SS | 14 | | Present | | Present | | | Present | |
| SC | 16 | | Present | Present | Present | | | Present | |
| AE | 10 | Present | | | Present | | | Present | Present |
| $AD^{Punjab}$ | 2 | Present | | | Present | Present | | Present | |
| $AO^{Arab}$ | 1 | Present | | | Present | | Present | Present | |
| CC | 1 | | | Present | Present | | | Present | |
| $D^{Punjab}D^{Punjab}$ | 1 | Present | | | | Present | | Present | |
| $O^{Arab}O^{Arab}$ | 1 | Present | | | | | Present | Present | |
| EE | 1 | Present | | | Present | | | | Present |

From table 5 it can be seen that the normal haemoglobin A phenotype would show the presence of the three wild type peptides T1, T13, T3 at their characteristic masses while sickle cell trait phenotype (AS) in addition to having peptides at these masses also has an ion at 472.4 Da. Similarly haemoglobin C trait phenotype (AC) shows a peptide at 694.4 Da in addition to the three wild type masses. We have shown this type of pattern to be true for the remaining trait phenotypes tested. In disease or compound heterozygote states the corresponding wild type peptide is absent with ionised peptides detected at the characteristic mass of the variant.

Figure 3:
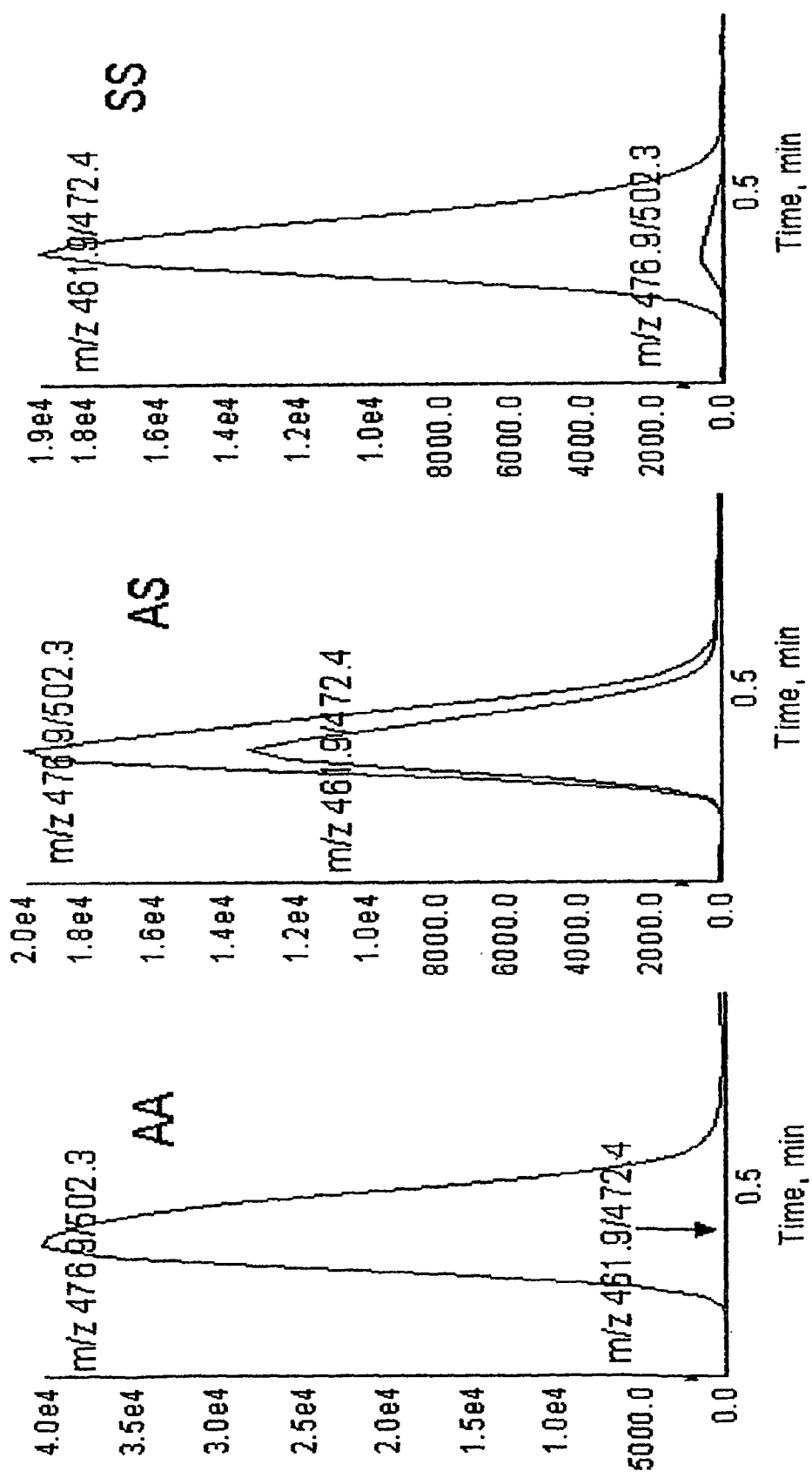
FIG. 3 shows the T1 peptide of beta globin—extracted MRM transitions m/z 476.9/502.3 (wild-type beta haemoglobin) and xn/z 461.9/472.4 (haemoglobin S) for control, sickle cell trait, and sickle cell disease.
Figure 4:
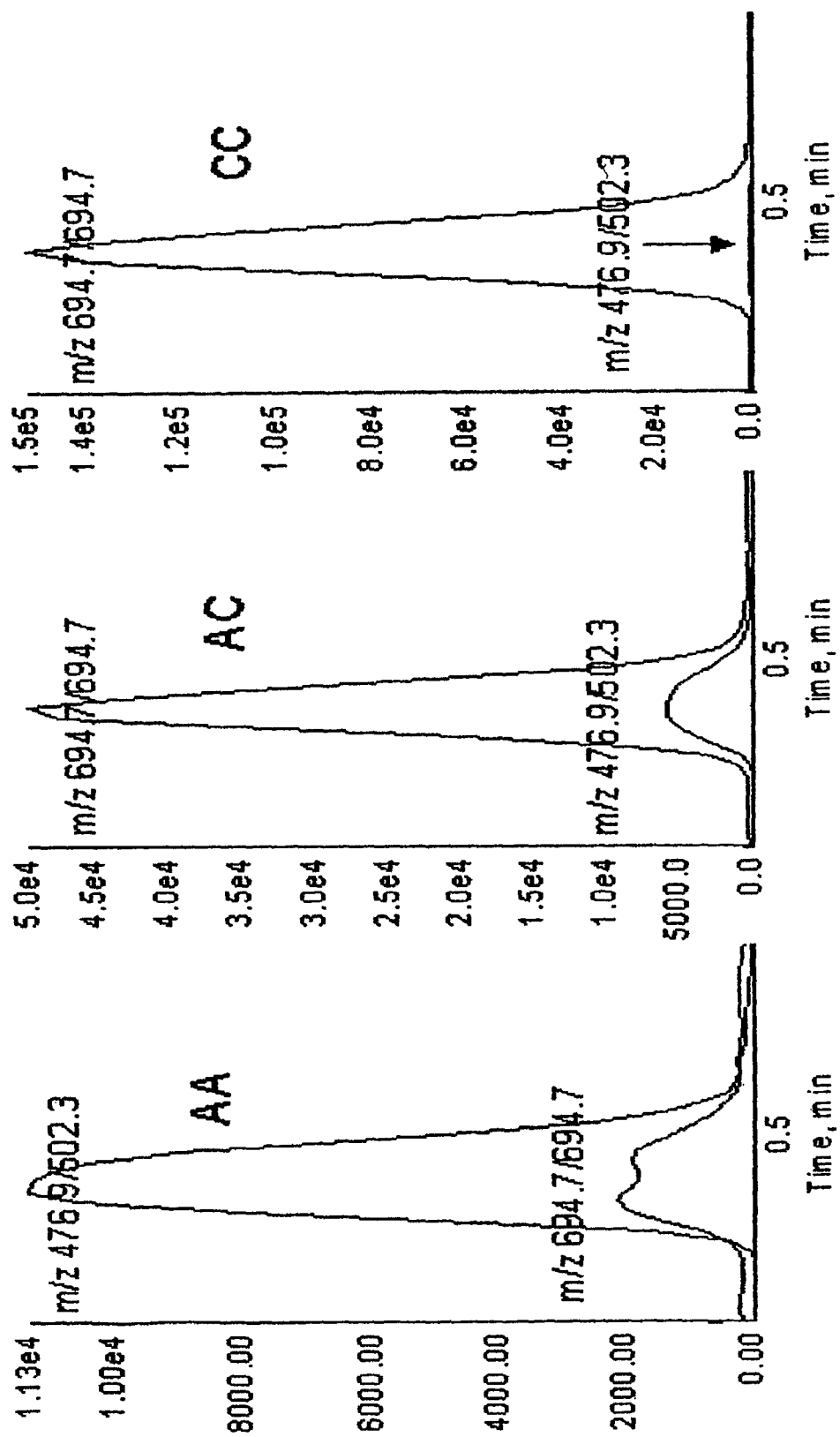
FIG. 4 shows the T1 peptide of beta globin—extracted MRM transitions m/z 476.9/502.3 (wild-type beta haemoglobin) and m/z 694.7/694.7 (haemoglobin C) for control, C trait, and C disease.
Figure 5:
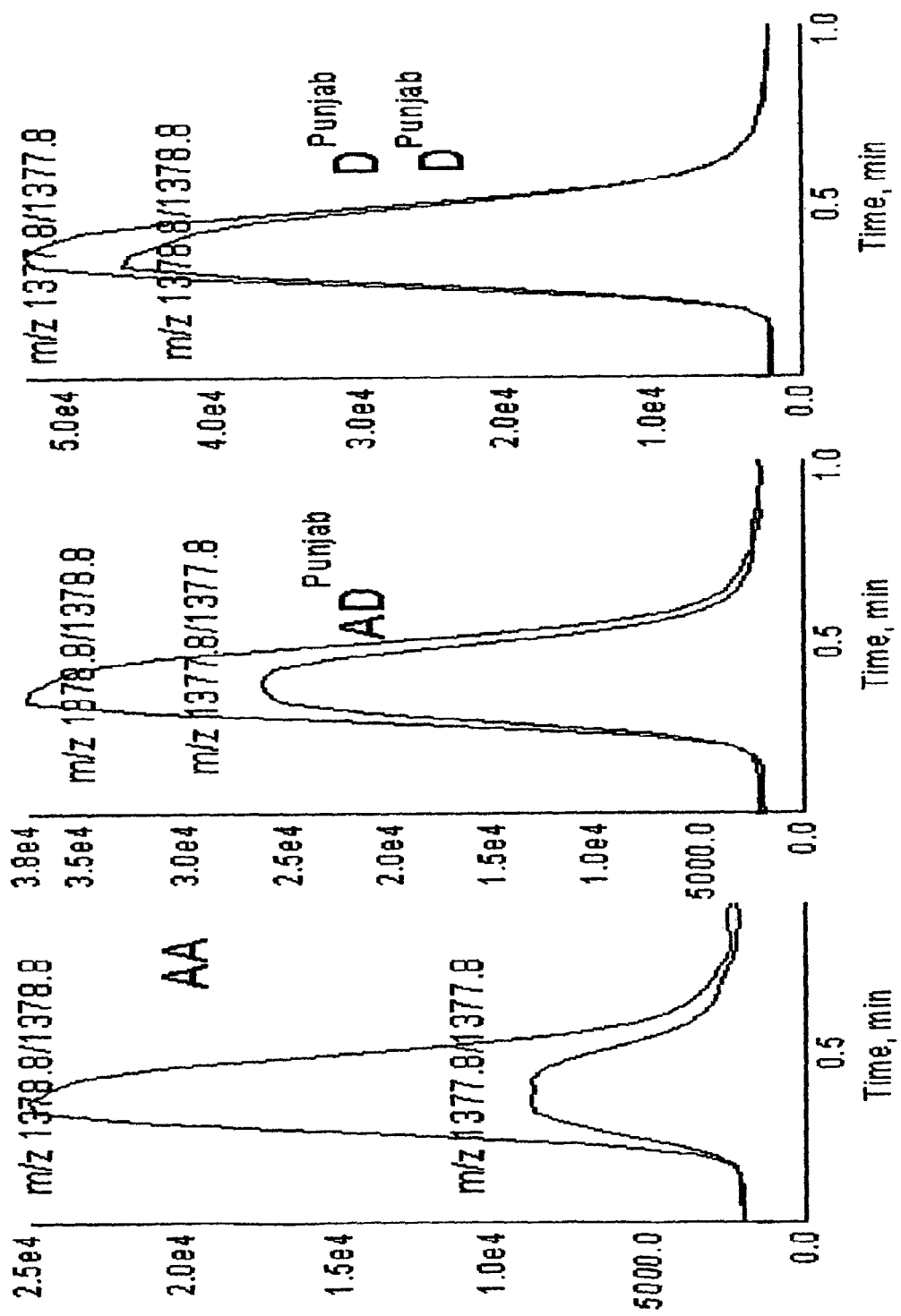
FIG. 5 shows the T13 peptide of beta globin—extracted MRM transitions m/z 1378.8/1378.8 (wild-type beta haemoglobin) and m/z 1377.8/1377.8 (haemoglobin $D^{Punjab}$) for control, $D^{Punjab}$ trait, and $D^{Punjab}$ disease.
Figure 6:
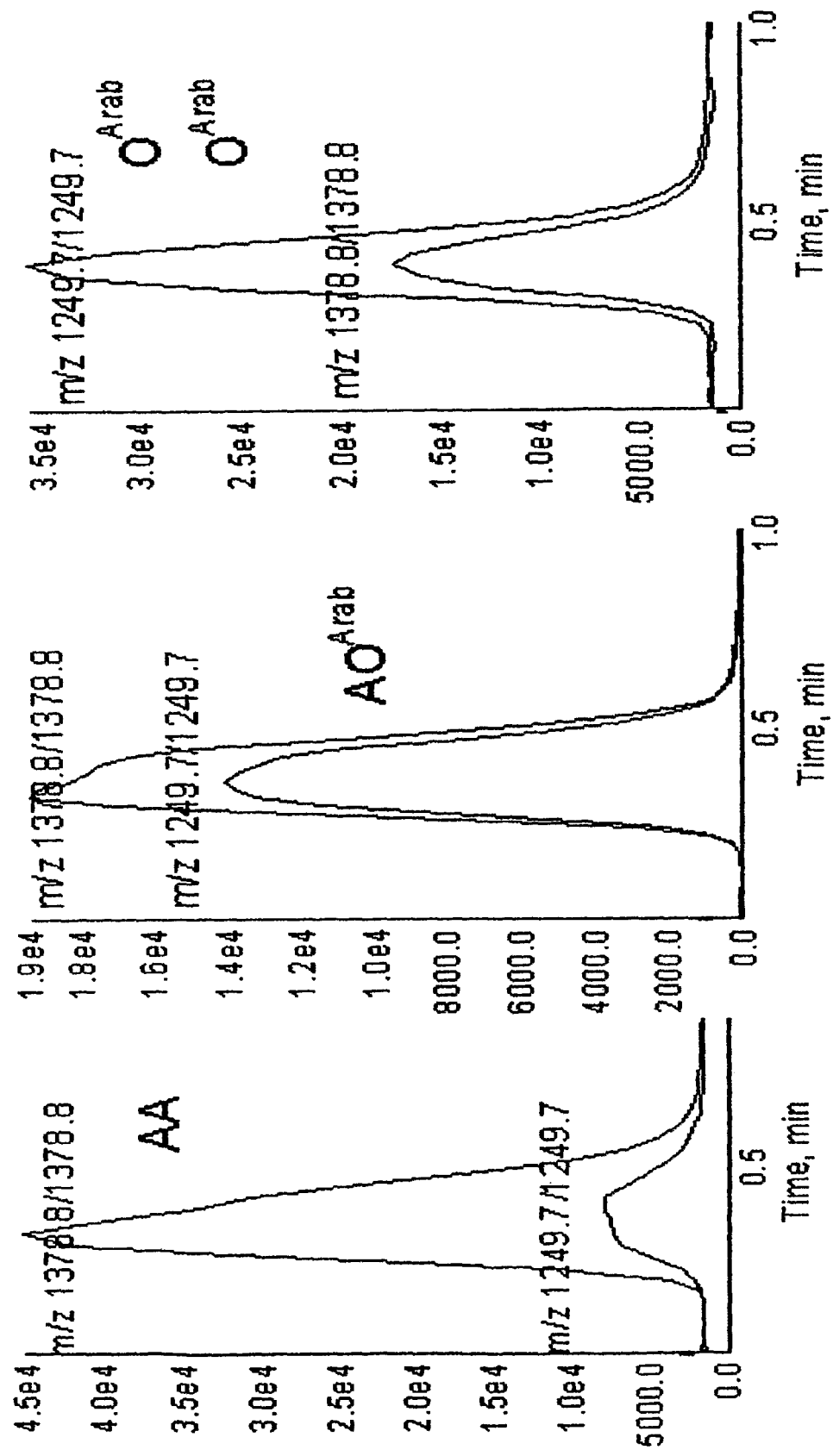
FIG. 6 shows the T13 peptide of beta globin—extracted MRM transitions m/z 1378.8/1378.8 (wild-type beta haemoglobin) and m/z 1249.7/1249.7 (haemoglobin $O^{Arab}$) for control, $O^{Arab}$ trait, and $O^{Arab}$ disease.
Figure 7:
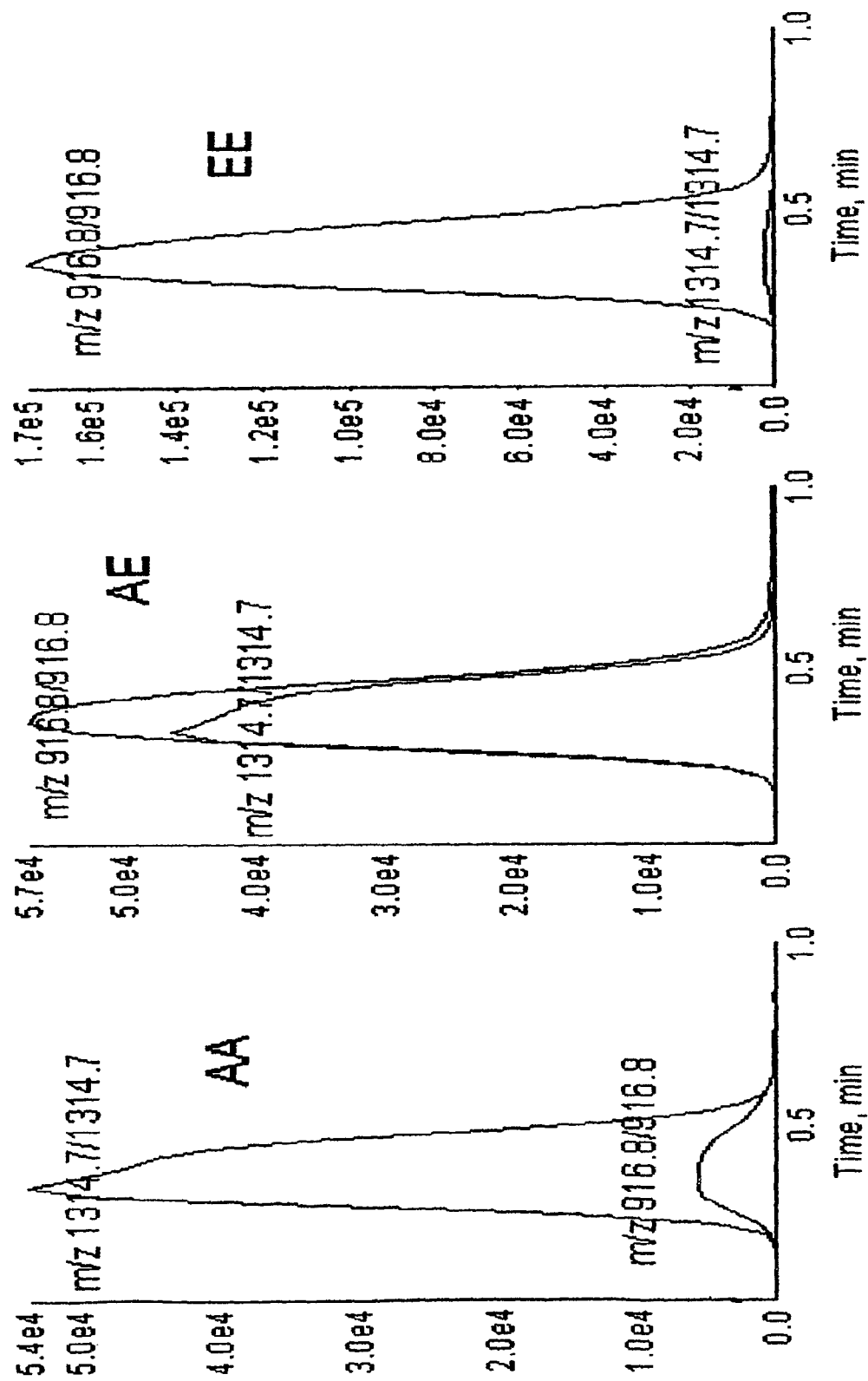
FIG. 7 shows the T3 peptide of beta globin—extracted MRM transitions m/z 1314.7/1314.7 (wild-type beta haemoglobin) and m/z 916.8/916.8 (haemoglobin E) for control, E trait, and E disease.

Four panels of data may be presented to the operator for each sample: the total ion chromatogram and then the T1, T13, and T3 peptides. For simplicity and to demonstrate the data effectively, T1 MRM data for samples from subjects with haemoglobins AA, AS, and SS are shown in FIG. 3. Note the virtual absence of S signal in the AA that results in a very high signal to noise ratio and hence sensitivity for S. Equivalent data for C, $D^{Punjab}$, $O^{Arab}$, and E are presented in FIGS. 4, 5, 6, and 7, respectively. Even using "pseudo-MRMs" the background signals are relatively small and simple visual inspection can identify heterozygote and homozygote status for all the mutations targeted. There is an apparently high wildtype signal for the T13 peptide even in patients homozygous for $D^{Punjab}$, due to the 1 Da shift. However, because of the relative ratios of the m/z 1377.8/1378.8 signals, detection of heterozygous and homozygous $D^{Punjab}$ are unaffected.

The inventors selected specimens to provide a cohort of those haemoglobin variants targeted in the testing protocol and have confirmed that all haemoglobin variants as identified by conventional techniques had the corresponding variant peptide detected by mass spectrometry. Furthermore as manner. A true screening programme aims "to identify those individuals within a population who have a specific disorder for which intervention, such as medical treatment, education or counselling, can improve the natural course of the disease" (Henthom et al., Br. J. Haematol. 124, 259-263, 2004). Current methods cannot truly be regarded as screening techniques as they detect a large number of haemoglobin variants many of which are not clinically significant. The specific identification of these variants currently undertaken by many laboratories is an ineffective use of limited resources. Furthermore existing methods have a relatively low through put, for example approximately 6 minutes per sample using some HPLC systems. Haemoglobins are provisionally identified by such systems and then require confirmation by other techniques before final validation of results (Wild, B. J., Bain, B. J. 2004 (supra)). Existing techniques of MSMS identification of haemoglobin variants are designed to definitively identify unknown haemoglobin variants (Wild et al, 2001 (supra)) and are effective but time consuming. Targeted screening for those haemoglobins deemed clinically significant within the programme will focus use of time and resources. A system capable of processing high numbers of samples and rapidly isolating required haemoglobin variants will cut down on turn around times and thereby reduce the time delay between specimen collection and patient counselling an important factor in ante-natal screening programmes.

The inventors have developed a novel strategy using tryptic digestion in conjunction with MSMS as a screening method for clinically significant haemoglobin variants. In devising this strategy the inventors decided to focus on haemoglobins S, C, E, $D^{Punjab}$ and $O^{Arab}$ since these represent a large proportion of the clinically significant haemoglobinopathies and samples were readily available within the laboratory. The inventors' intention was to develop a true screening programme. Analysis of the intact beta chain is not informative for haemoglobins C, E, D$^{Punjab}$ and O$^{Arab}$ that have a mass shift of only 1 Da from wild type. Haemoglobin S has a mass shift of 30 Da and although this would be detected when analysing intact beta chains it cannot be regarded as specific. In order to improve this specificity and so that the other haemoglobins can be detected it is necessary to break the beta chain into smaller peptides. This adds to laboratory process but can be automated. Using trypsin the beta chain is broken into 15 peptides; T1, T3 and T13 were chosen as containing the mutations of interest. As described in the methods section the digested sample was analysed using electrospray MSMS to determine which of the multiply charged ionised peptides was most suitable for selection as the ionised peptide target. The choice of target ionised peptide requires consideration of any other potential amino acid substitutions that may affect specificity. In particular a potential problem occurs in the T1 peptide where a wild type glutamic acid to valine substitution at position 6 results in haemoglobin S with a mass shift of −30 Da. Two other possible amino acid substitutions in this T1 peptide give the same mass shift; firstly wild type threonine to alanine at position 4 and secondly wild type glutamic acid to valine at position 7. Neither of these substitutions has currently been reported, although two others at the position 7 glutamic acid have been. Here a glycine substitution results in a mass shift of −72 Da (haemoglobin G-San Jose) whilst a lysine substitution results in a mass shift of −1 Da (haemoglobin G-Siriraj). Neither of these haemoglobins is clinically significant and would not be detected by the protocols described.

In setting up the haemoglobin S protocol it was necessary to select the transitions to give the optimum signal/specificity compromise. The [M+2H] ionised peptide provides the best signal and for this reason was selected from the multiply charged peptide ions in MS 1. To select the most suitable derived ionised species for analysis in MS 2 a choice must be made between either the b ion or the y ion. Unfortunately from the b terminal end the beta chain position 4 threonine to alanine mutation is possible and from the y terminal end the beta chain position 7 glutamic acid to valine mutation is possible. Should either of these mutations occur they could generate a false positive with this protocol. This means with neither the b ion nor the y ion can a selection be made to exclude a mutation that may affect the specificity. Thus the derived ionised species of choice could be either the b6 fragment or y3 fragment because these correspond to the mutation position. In practice no y3 fragment was detected and the b6 fragment was not chosen because the signal generated was poor. Ultimately the y4 fragment was chosen because it gave a single clear ion of good abundance and being a small peptide there is a limited capacity for multiple mutations. These may result in reduced specificity by generating a combined mass shift of −30 Da although analysis of this peptide sequence indicates that no double mutation would cause such a mass shift.

The stated requirements of the United Kingdom National Health Service Haemoglobinopathy neonatal screening programme imply that, as a minimum in the initial screening phase, detection of haemoglobin S and/or demonstrating a deficiency of wild-type beta-globin should be sufficient[4]. Heterozygote or homozygote status can be determined and other sickling mutations characterised at the confirmatory testing stage. The confounding problem in neonatal screening is the very low expression of beta-globin in neonates, particularly those that are premature. It is essential, therefore, to have a very sensitive screening method for detecting haemoglobin S. Using the specific MRM transition for haemoglobin S the non-specific background signal found in a haemoglobin AA subject (FIG. 3) indicates that even levels of haemoglobin S representing significantly less than 1% of total haemoglobin will be detectable. Although, not strictly essential, the current approach also enables detection and confirmation of the other sickling mutations in the original tryptic digest.

The remaining haemoglobin variants generate peptides that are specific in the presence of a single mutation in that peptide. These are analysed using protocols the inventors have termed pseudo MSMS. In these the ionised peptide is selected in MS 1 and then re-selected in MS 2 after passing through the collision chamber with gas flowing. This may cause fragmentation of any isobaric peptides that may have passed through MS 1 ensuring that MS 2 will not select them. Analysis without gas gives significantly increased background signal as well as giving reduced signal on some of the target fragments.

The potential of this method for neonatal haemoglobinopathy screening has already been discussed but this approach may prove even more valuable in ante-natal screening programmes. The major difference between neonatal and ante-natal screening is that in the latter it is essential that heterozygotes for compound sickling mutations be detected. At present we have not described a comprehensive system for ante-natal screening but we have demonstrated how successful the approach is in detecting heterozygotes for the majority of the compound sickling mutations. The process is not restricted to the beta chain and could be extended to include any other mutations of clinical interest and provide a comprehensive approach to clinical haemoglobinopathy characterisation and diagnosis. Furthermore, when the clinical picture suggests a haemoglobinopathy, but the targeted mutations are all normal, the MSMS is still available to do a classical sequence analysis.

CONCLUSION

The inventors have developed a protocol suitable for high throughput analysis that rapidly and specifically screens for targeted haemoglobin variants. This initial in parallel investigation, with existing methods, shows 100% concordance with the 200 samples selected.

Detection of Delta Beta Thalassaemia

The method of the present invention has also been used to detect Delta Beta Thalassaemia (also referred to as Beta Thalassaemia).

It is fifty years since Haemoglobin (Hb) $A_2$ was first described using starch gel electrophoresis, as the second normal haemoglobin to be identified in the blood of normal adults. Haemoglobin Hb $A_2$ was found to be normally present at approximately 3 percent, however, studies of the concentration in different ages and disease states revealed that Hb $A_2$ was absent or greatly reduced in neonates and characteristically raised in thalassaemia trait. It was later postulated that elevation of Hb $A_2$ would most likely be a feature in beta thalassaemia as decreased beta chain synthesis would result in a relative increase in the proportion of Hb. Increased levels of Hb $A_2$ have now become regarded as a characteristic diagnostic feature of beta thalassaemia trait and are used to differentiate from alpha thalassaemia trait. Diagnosis of beta thalassaemia trait is of key importance in genetic counselling as when inherited as a homozygous condition or in conjunction with other haemoglobinopathies it results in a clinically severe condition.

Methods for quantifying Hb $A_2$ require separation of Hb $A_2$ from any other haemoglobins present and determining the proportion present. Three techniques can be employed: haemoglobin electrophoresis and subsequent elution of the haemoglobin bands; micro column chromatography; or automated high performance liquid chromatography (HPLC). Elution and column chromatography methods are time consuming and laborious, leading to selective screening policies based on abnormal red cell indices. However, the introduction of automated HPLC systems in the 1990's has facilitated mass screening of Hb $A_2$ levels. This approach is applicable for screening of beta thalassaemia trait in population screening programmes. The benefits of screening by HPLC include simultaneous identification and quantitation of Hb $A_2$ and other normal and abnormal haemoglobins, as well as identification of patients that may have been missed by previous screening policies. This includes those with beta thalassaemia trait but normal red cell indices and those with delta chain variants. HPLC systems may however give erroneous results for Hb $A_2$ in the presence of some haemoglobin variants (Wild et al., Ann. Clin. Biochem., 41, 355-369, 2004).

Whilst raised Hb $A_2$ levels (range 4-7%) in the presence of hypochromic, microcytic red cell indices are almost invariably due to beta thalassaemia trait, elevated Hb $A_2$ levels have also been reported in other situations including normal patients, unstable haemoglobins, hyperthyroidism, megaloblastic anaemia and human immunodeficiency virus infected patients on anti-retroviral therapy. Other problems associated with Hb $A_2$ include borderline normal and equivocal values in the range of 3.5-3.9%. Again such values may be found in normal patients but may also be caused by mild beta thalassaemia mutations such as the −101 C→ and +1 CAP site A→C or environmental factors which may reduce the Hb $A_2$ level such iron deficiency and co-inherited alpha thalassaemia trait. Due to the fact that levels do not reach adult values until at least 6 months of age Hb $A_2$ is not a useful marker for beta thalassaemia trait in neonates. However, despite these points, in conjunction with red cell indices, Hb $A_2$ remains the standard marker for beta thalassaemia screening in adults.

Haemoglobin Lepore was first reported in 1957 due to its interaction with beta thalassaemia trait to produce a clinical picture similar to that of thalassaemia major. Hb Lepore Trait is characterised by the reduced red cell indices found in thalassaemia trait and the presence of Hb Lepore at 10 to 15 percent of the total haemoglobin. Hb Lepore is produced as a result of fusion of the delta and beta genes. Three Lepore variants have been described with the same electrophoretic mobility however the point at which fusion of the delta and beta genes occurs is different in each. Detection of Hb Lepore is essential in population screening programmes due to the interaction with beta thalassaemia trait to produce a clinically significant condition.

In ante-natal screening it is also important to detect beta thalassaemia trait. As described, this has been traditionally achieved using Hb $A_2$ which has two beta and two delta globin chains. In this method the inventors have investigated detection of the delta chain by MSMS to determine the utility as a surrogate marker. This approach also allows the detection of delta beta fusions (Hb Lepore variants) and gamma beta fusions. Using an identical approach to that described above, the inventors report additional transitions within the one minute cycle time, using delta chains as a surrogate Hb $A_2$ with the objective of detecting beta thalassaemia trait and Hb Lepore.

Materials and Methods

MSMS Strategy

There is strong sequence homology between the beta and delta chains of haemoglobin. Tryptic digest of the beta chain produces a series of 15 well defined peptides, similarly the delta chain produces a series of 16 (T1-T16) peptides with differences from beta in T2, T3, T5, T10, T12, T13 and T14. The first sequence difference occurs in the T2 peptide which comprises amino acids 9 to 17 in both the beta and delta chains with respective sequences of SAVTALWGK (SEQ ID NO:9), average mass 932.1 daltons (da) and TAVNALWGK (SEQ ID NO:10), average mass 959.1 da. In multiple reaction monitoring mode (MRM), as described above, the respective T2 $[M+2H]^2$ ions, mass to charge ratio (m/z) beta, 466.8 and delta, 480.3 were selected, fragmented and the most informative peptide fragments VTALWGK (SEQ ID NO:11), 675.4 da and VNALWGK (SEQ ID NO:12), 688.4 da, targeted. The percentage area ratio of delta/(beta+delta) was calculated and compared with the classical percentage HbA2 value obtained by HPLC. 66 samples with Hb A2 values within our normal range (mean 2.65%, range 1.8-3.4), and 58 with HbA2 values indicative of beta thalassaemia trait (5.24%, 4.2-7.9) were analysed by MSMS and the corresponding delta/(beta+delta) ratios were 1.7%, 0.9-2.3 and 3.4%, 2.5-6.0. In 2 further HbS beta thalassaemia zero compound heterozygote samples, confirmed by beta gene sequencing, the ratios were 4.1% and 3.7%. This relatively small series provides evidence that beta thalassaemia trait may be diagnosed by MSMS.

A further advantage of this approach is that any Lepore variant will have a high T2 signal. Unfortunately the most common delta chain variant Hb $A'_2$ (Hb $B_2$) occurs at position 16 of the delta globin chain and therefore falls within this peptide.

In order not to miss beta thalassaemia trait with a concomitant delta chain variant the next informative peptide (i.e., T3 beta sequence VNVDEVGGEALGR (SEQ ID NO:13) average mass 1314.4 da and delta sequence VNVDAVGGEALGR (SEQ ID NO:14), average mass 1256.4 da) was included for assessment. In MRM the respective T3 $[M+2H]^{2+}$ ions m/z beta, 657.9 da and delta, 628.9 da were selected, fragmented and the singly charged ions of two series within the T3 peptide were detected. The series are as follows transition 1, beta, EVGGEALGR (SEQ ID NO:15), m/z 887.5 da, delta, AVGGEALGR (SEQ ID NO:16), m/z 829.5 da, transition 2, beta AVGGEALGR (SEQ ID NO:17), m/z 758.4 da, delta, VGGEALGR (SEQ ID NO:18), m/z 758.4 da.

Although rare the potential problem of delta chain variants occurring at any point in the delta chain sequence implied that a third peptide could prove valuable in data interpretation. Initially the T13 delta peptide was targeted. This peptide comprises amino acids 117 to 120 of the delta chain, sequence NFGK, average mass 464.5 da. The small number of amino acids was considered advantageous as it limits the possibility of mutations, however the signal detected from this peptide was too low for analysis. The complementary T13 beta sequence, comprises amino acids 121 to 132, sequence EFTPPVQAAYQK (SEQ ID NO: 19), average mass 1378.5 da. Thus the T14 delta peptide is also complementary to this sequence and was selected for analysis, sequence EFTPQMQAAYQK (SEQ ID NO:20), average mass 1441.6 da. This peptide has the advantage of being at the N terminal end and is the last peptide with differences between the delta and beta sequences. Thus selection of this peptide in conjunction with the T2 peptide covers both ends of the delta chain. In MRM the $[M+2H]^{2+}$ ions, for T13 beta, m/z 689.9 da and T14 delta, 501.3 da are selected, fragmented and the doubly charged ions of the respective informative peptide fragments PPVQAAYQK (SEQ ID NO: 21), 501.3 da and PQM-QAAYQK (SEQ ID NO:22), 532.9 da are detected and measured.

Blood Spots

A total of 26 blood spot samples were analysed. These comprised 13 with a normal Hb $A_2$, 11 with a raised Hb $A_2$ (beta thalassaemia trait) and two delta chain variants.

Materials for Trypsin Digestion and MSMS Analysis

Ammonium bicarbonate (A6141), TCPK treated trypsin (T1426), and 88% formic acid (39,938-8) (Sigma Aldrich Co Ltd, Dorset, UK). HPLC grade acetonitrile (RH1015) (Rathburn Chemicals Ltd, Scotland).

Standard Methods for Haemoglobin A2 Quantitation and Hb Lepore Identification

Whole Blood

The Guideline, laboratory diagnosis of haemoglobinopathies was taken as minimum standard. The haemoglobinopathy screen and Haemoglobin A2 quantitation was performed by high performance liquid chromatography (HPLC) using a Variant™ II operating with $HbA_2/HbA_{1c}$ Dual Program kit (Bio-Rad Laboratories Ltd, Hemel Hempstead, UK). Haemoglobin Lepore variants were initially detected by HPLC and confirmed by mass spectrometry (Wild et al, 2001 (supra)).

Blood Spots

Whole blood EDTA specimens were analysed by HPLC and mass spectrometry. For each sample seven blood spots were then made pipetting 35 μl of blood per spot onto Schleicher and Schuell 903 filter paper. The blood spots were allowed to dry over night and punched and analysed by both HPLC and mass spectrometry at day one, day eight and day 29. For HPLC two punched spots were eluted for 90 minutes into 1 ml of Bio-Rad wash buffer (Bio-Rad Laboratories Ltd, Hemel Hempstead, UK) giving the equivalent of the 1:201 dilution required for standard analysis.

Controls and Standards

The WHO international reference reagent for Haemoglobin $A_2$ obtained from the National Institute of Biological Standards and Controls was used as a standard. A series of controls were obtained from Canterbury Scientific, New Zealand, these comprised a Hb $A_2$/Hb F normal and high, Hb $A_2$ normal and high and an Hb FASC. All controls were prepared, reconstituted and stored as per manufacturers instructions. Once reconstituted the controls were treated as whole blood samples.

Sample Preparation for MSMS

Whole Blood

Following the method described by Wild et al, 2001 (supra), and as described above.

Blood Spots

A working solution was created by punching one 3 mm spot into 200 μl of deionised water and eluting for 30 minutes on an automated mixer, 100 μl of this solution was then processed as described.

Mass Spectrometry

MSMS was performed as described above. The total acquisition time remained at 60 sec.

Results

Using MSMS all bloods with raised A2 values were clearly distinguished from those with normal A2 values. This did not change on storage as dried blood spots for 1 day, 8 days or 21 days. The HPLC data has not yet been reviewed.

DISCUSSION

Prior to the introduction of HPLC based methods in the 1990's techniques for quantitating Hb $A_2$ were laborious and time consuming. HPLC has enabled high throughput screening for haemoglobin variants and beta thalassaemia to be carried out on a routine basis and lead to a rapid rise in population screening programmes. However, due to differences in sample materials and the operating programmes utilised, neonatal blood spot and adult whole blood screening are carried out on different platforms. Approved screening methods for neonates include HPLC and isoelectric focusing (IEF), whilst HPLC is the only approved method for adults (Department of Health, UK, 2000; NHS Sickle Cell and Thalassaemia Screening Programme, 2005). The neonate blood spot HPLC platform requires specialist instrumentation and methodology different to that used for adult screening. LEF is not suitable as a screening method for beta thalassaemia trait as it does not permit Hb $A_2$ measurement.

The technique we have described specifically detects and quantitates the delta chain rather than Hb $A_2$ (a combination of two alpha and two delta chains). One advantage of targeting the delta chain is that it is possible to detect and quantitate even in the presence of factors which may prevent or interfere with Hb $A_2$ quantitation using traditional methods. For example, variants that co-elute with Hb $A_2$ or the presence of Hb S, which in some HPLC systems give rise to falsely elevated Hb $A_2$ values.

When a delta chain mutation leading to the formation of a delta chain variant is present the effect on the Hb $A_2$ is to reduce the value to approximately half. It is important to obtain a total Hb $A_2$ by adding together the amount of the variant and the normal Hb $A_2$ in order to ensure that a diagnosis of beta thalassaemia trait is not missed. Selection of two delta peptide transitions ensures that delta chain heterozygotes and homozygotes would not be missed by this technique. It is possible for a person to inherit two different delta chain mutations and, although this would undoubtedly be a rare occurrence, in this study we have chosen to analyse three transitions to measure the delta chain signal. This approach ensures that even in the unlikely event of a compound heterozygote delta chain mutation, one of the transitions should still give the correct value. Whilst for routine screening purposes this may be deemed to be excessive, it is worth noting that increasing the number of acquisitions does not increase the analysis time but does allow for further specificity and sensitivity.

The most common delta chain mutation occurs in the T2 peptide of the delta chain and whilst there may be an argument towards not using this peptide it is essential if the detection of haemoglobin Lepore variants is a requirement. The three Lepore variants are all the result of a delta beta fusion and posses delta sequences as follows: Hb Lepore-Hollandia delta sequence through to amino acid 22; Hb Lepore Baltimore delta through to amino acid 50; and Hb Lepore Boston Washington delta through to amino acid 87. Theoretically there should an increase of the delta peptides prior to the fusion point which could be detected and quantified by MSMS provided the appropriate peptide fragment is targeted. In order to detect all of the Hb Lepore variants a peptide with differences from the beta sequence prior to peptide 22 must be selected and T2 is the only peptide which fulfils this requirement. Thus the T2 peptide selected for delta chain quantitation was also used to detect the Hb Lepore variants.

All documents cited above are incorporated herein by reference.

The invention claimed is:

1. A method for detecting a known protein variant in a sample, wherein the sequence of the protein variant to be detected is known, the method comprising:
    (i) digesting the protein to produce a defined series of peptides;
    (ii) ionising the peptides and selecting by mass spectrometry an ionised species of known mass/charge ratio indicative of the protein variant;
    (iii) subjecting the selected ionised species to collision induced dissociation to form a derived ionised species of known mass/charge ratio; and
    (iv) measuring the derived ionised species of known mass/charge ratio by scanning a window of mass/charge ratios that consists essentially of the known mass/charge ratio of the derived ionised species, wherein presence of the derived ionised species in the window confirms the presence of the protein variant in the sample.

2. The method of claim 1, wherein the protein variant is a haemoglobin variant.

3. The method of claim 2, wherein the haemoglobin variant is S, $C_5$ E, $D^{punjab}$ or $O^{arab}$.

4. The method of claim 2, wherein the protein variant is the delta chain of haemoglobin.

5. The method of any one of the preceding claims, wherein in step (ii) 1 to 20 ionised species of known mass/charge ratio are selected.

6. The method of claim 5, wherein in step (ii) 1 to 5 ionised species of known mass/charge ratio are selected.

7. The method of claim 6, wherein in step (ii) a single ionised species having a known mass/charge ratio is selected.

8. The method according to claim 1, wherein the sample is blood, urine, cerebrospinal fluid or a tissue sample.

9. The method of claim 1, wherein the protein is digested using a sequence specific protease.

10. The method of claim 9, wherein the protease is trypsin.

11. The method according to claim 1, wherein electrospray ionisation quadrupole mass spectrometry is used to ionise the peptides and to select the ionised species.

12. The method according to claim 1, wherein electrospray ionisation quadrupole mass spectrometry is used to subject the selected ionised species to collision induced dissociation and to measure the single derived ionised species.

13. The method of claim 1, wherein the selected ionised species is subjected to a level of dissociation that leads to the production of a plurality of ionised peptide fragments.

14. The method of claim 1, wherein the sample is a whole blood sample or a dried blood spot and the step of digesting the protein is performed on the sample.

15. A method for detecting a known protein variant in a sample, wherein the sequence of the protein variant to be detected is known, the method comprising:
    (i) digesting the protein to produce a defined series of peptides;
    (ii) ionising the peptides and selecting by mass spectrometry an ionised species of known mass/charge ratio indicative of the protein variant by scanning a window consisting essentially of the mass/charge ratio of the ionised species;
    (iii) subjecting the selected ionised species to collision induced dissociation to form a derived ionised species of known mass/charge ratio; and
    (iv) measuring the derived ionised species of known mass/charge ratio by scanning a window of mass/charge ratios that consists essentially of the known mass/charge ratio of the derived ionised species, wherein presence of the derived ionised species in the window confirms the presence of the protein variant in the sample, wherein only a limited window of mass/charge ratios is scanned.

16. The method according to claim 15, wherein the window of mass/charge ratios scanned when measuring the presence of the derived ionised species consists of the specific known mass/charge ratio of the single derived ionised species.

* * * * *

SEQUENCE LISTING

<160> NUMBER OF SEQ ID NOS: 21

<210> SEQ ID NO 1
<211> LENGTH: 6
<212> TYPE: PRT
<213> ORGANISM: Homo sapiens

<400> SEQUENCE: 1

Val His Leu Thr Pro Lys
 1               5

<210> SEQ ID NO 2
<211> LENGTH: 12
<212> TYPE: PRT
<213> ORGANISM: Homo sapiens

<400> SEQUENCE: 2

Glu Phe Thr Pro Pro Val Gln Ala Ala Tyr Gln Lys
 1               5                  10

<210> SEQ ID NO 3
<211> LENGTH: 12
<212> TYPE: PRT
<213> ORGANISM: Homo sapiens

<400> SEQUENCE: 3

Gln Phe Thr Pro Pro Val Gln Ala Ala Tyr Gln Lys
 1               5                  10

<210> SEQ ID NO 4
<211> LENGTH: 12
<212> TYPE: PRT
<213> ORGANISM: Homo sapiens

<400> SEQUENCE: 4

Glu Phe Thr Pro Pro Val Gln Ala Ala Tyr Gln Lys
 1               5                  10

<210> SEQ ID NO 5
<211> LENGTH: 11
<212> TYPE: PRT
<213> ORGANISM: Homo sapiens

<400> SEQUENCE: 5

Phe Thr Pro Pro Val Gln Ala Ala Tyr Gln Lys
 1               5                  10

<210> SEQ ID NO 6
<211> LENGTH: 13
<212> TYPE: PRT
<213> ORGANISM: Homo sapiens

<400> SEQUENCE: 6

Val Asn Val Asp Glu Val Gly Gly Glu Ala Leu Gly Arg
 1               5                  10

<210> SEQ ID NO 7
<211> LENGTH: 13
<212> TYPE: PRT
<213> ORGANISM: Homo sapiens

<400> SEQUENCE: 7

Val Asn Val Asp Glu Val Gly Gly Lys Ala Leu Gly Arg
 1               5                  10

```
<210> SEQ ID NO 8
<211> LENGTH: 9
<212> TYPE: PRT
<213> ORGANISM: Homo sapiens

<400> SEQUENCE: 8

Val Asn Val Asp Glu Val Gly Gly Lys
1               5

<210> SEQ ID NO 9
<211> LENGTH: 9
<212> TYPE: PRT
<213> ORGANISM: Homo sapiens

<400> SEQUENCE: 9

Ser Ala Val Thr Ala Leu Trp Gly Lys
1               5

<210> SEQ ID NO 10
<211> LENGTH: 9
<212> TYPE: PRT
<213> ORGANISM: Homo sapiens

<400> SEQUENCE: 10

Thr Ala Val Asn Ala Leu Trp Gly Lys
1               5

<210> SEQ ID NO 11
<211> LENGTH: 7
<212> TYPE: PRT
<213> ORGANISM: Homo sapiens

<400> SEQUENCE: 11

Val Thr Ala Leu Trp Gly Lys
1               5

<210> SEQ ID NO 12
<211> LENGTH: 7
<212> TYPE: PRT
<213> ORGANISM: Homo sapiens

<400> SEQUENCE: 12

Val Asn Ala Leu Trp Gly Lys
1               5

<210> SEQ ID NO 13
<211> LENGTH: 13
<212> TYPE: PRT
<213> ORGANISM: Homo sapiens

<400> SEQUENCE: 13

Val Asn Val Asp Glu Val Gly Gly Glu Ala Leu Gly Arg
1               5                   10

<210> SEQ ID NO 14
<211> LENGTH: 13
<212> TYPE: PRT
<213> ORGANISM: Homo sapiens

<400> SEQUENCE: 14

Val Asn Val Asp Ala Val Gly Gly Glu Ala Leu Gly Arg
1               5                   10

<210> SEQ ID NO 15
```

```
<211> LENGTH: 9
<212> TYPE: PRT
<213> ORGANISM: Homo sapiens

<400> SEQUENCE: 15

Glu Val Gly Gly Glu Ala Leu Gly Arg
1               5

<210> SEQ ID NO 16
<211> LENGTH: 9
<212> TYPE: PRT
<213> ORGANISM: Homo sapiens

<400> SEQUENCE: 16

Ala Val Gly Gly Glu Ala Leu Gly Arg
1               5

<210> SEQ ID NO 17
<211> LENGTH: 8
<212> TYPE: PRT
<213> ORGANISM: Homo sapiens

<400> SEQUENCE: 17

Val Gly Gly Glu Ala Leu Gly Arg
1               5

<210> SEQ ID NO 18
<211> LENGTH: 12
<212> TYPE: PRT
<213> ORGANISM: Homo sapiens

<400> SEQUENCE: 18

Glu Phe Thr Pro Pro Val Gln Ala Ala Tyr Gln Lys
1               5                   10

<210> SEQ ID NO 19
<211> LENGTH: 12
<212> TYPE: PRT
<213> ORGANISM: Homo sapiens

<400> SEQUENCE: 19

Glu Phe Thr Pro Gln Met Gln Ala Ala Tyr Gln Lys
1               5                   10

<210> SEQ ID NO 20
<211> LENGTH: 9
<212> TYPE: PRT
<213> ORGANISM: Homo sapiens

<400> SEQUENCE: 20

Pro Pro Val Gln Ala Ala Tyr Gln Lys
1               5

<210> SEQ ID NO 21
<211> LENGTH: 9
<212> TYPE: PRT
<213> ORGANISM: Homo sapiens

<400> SEQUENCE: 21

Pro Gln Met Gln Ala Ala Tyr Gln Lys
1               5
```